United States Patent [19]

Gedeon et al.

[11] 4,200,094

[45] Apr. 29, 1980

[54] APPARATUS FOR WARMING AND MOISTENING A RESPIRATION GAS

[75] Inventors: Andras Gedeon, Täby; Sven-Gunnar Olsson, Sollentuna; Georgios Psaros, Norsborg, all of Sweden

[73] Assignee: Siemens Aktiengesellschaft, Berlin & Munich, Fed. Rep. of Germany

[21] Appl. No.: 883,125

[22] Filed: Mar. 3, 1978

[30] Foreign Application Priority Data

Apr. 5, 1977 [DE] Fed. Rep. of Germany ....... 2715228

[51] Int. Cl.$^2$ ............................................ A61M 16/00
[52] U.S. Cl. ................................................ 128/201.13
[58] Field of Search ............... 128/212, 186, 188, 192, 128/193, 194; 55/387, 159, 57, 58, 59; 261/105, 106, 107, 96

[56] References Cited

U.S. PATENT DOCUMENTS

| | | | |
|---|---|---|---|
| 2,926,747 | 3/1960 | Wright et al. ...................... | 55/387 X |
| 3,854,907 | 12/1973 | Rising ................................... | 55/159 |
| 4,063,913 | 12/1977 | Kippel et al. ..................... | 128/188 X |

FOREIGN PATENT DOCUMENTS 2611898   9/1976   Fed. Rep. of Germany ........... 128/188

Primary Examiner—Henry J. Recla
Attorney, Agent, or Firm—Hill, Van Santen, Steadman, Chiara & Simpson

[57] ABSTRACT

In the illustrated embodiment, the moisture reservoir comprises a tube of gas-permeable, hygroscopic material. The exhalation flow path is into a blind axial bore of a spool like member having a series of transverse notches or cuts at the top and bottom which provide interspaces leading from the bore to the tube which covers the notches at their periphery. The notches leave integral fins or lamellae with large surface area exposed to the in-flow of dry respiration gas radially through the tube wall and into the interspaces which provide further reservoirs for moisture and warmth.

4 Claims, 1 Drawing Figure

U.S. Patent  Apr. 29, 1980  4,200,094
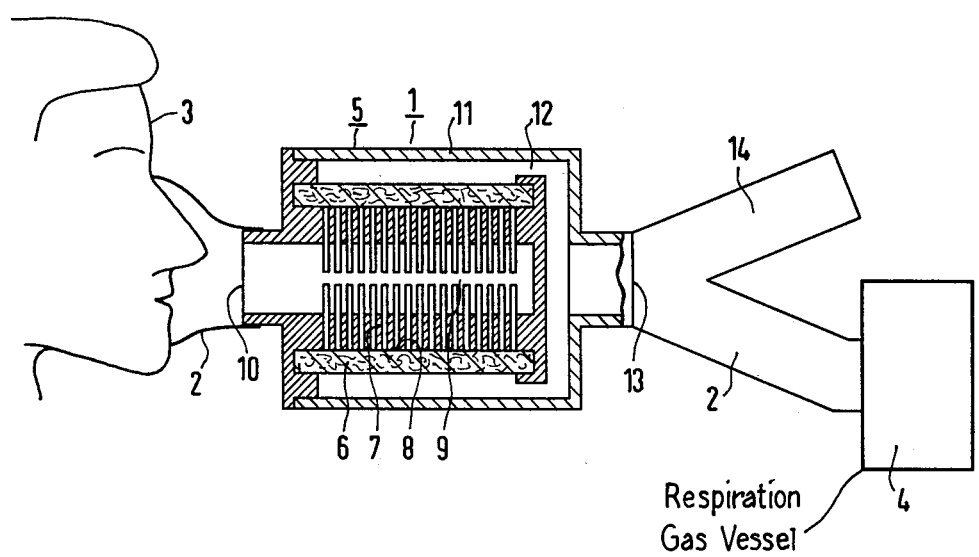

APPARATUS FOR WARMING AND MOISTENING A RESPIRATION GAS

BACKGROUND OF THE INVENTION

The invention relates to an apparatus for warming and moistening a respiration gas for a patient, comprising, in a housing disposed in a gas line leading to the patient and to a respiration gas vessel, a moisture reservoir consisting of gas-permeable, hygroscopic material.

There is an apparatus of this type known in which the moisture reservoir or store consists of a roller paper strip, the longitudinal axis of the roll being arranged in the direction of flow of the respiration gas. The moisture and warmth of the gas exhaled by the patient is stored in the air gaps between the paper layers of the roll. Furthermore, the paper absorbs part of the moisture and also stores part of the warmth. As the patient inhales, the inhalation gas is warmed and moistened as it passes the roll. This apparatus is unable to store enough warmth and moisture from the exhalation gas to warm and moisten adequately very dry respiration gas, e.g. in respirator treatments.

Further known in an apparatus for warming and moistening a dry respiration gas supplied to a patient which has a vessel filled with warm water, in which the inhalation gas is conveyed through the water. The gas is thereby warmed and receives a high degree of atmospheric moisture. Because of its construction, this apparatus must be disposed at a comparatively great distance from the patient such that the respiration gas in the connection line to the patient can cool down again. Furthermore, condensation water may form there. To avoid this, the connection line can be warmed in dependence on the temperature of the respiration gas measured at the patient's mouth. This produces a bulky, expensive and structurally complicated design.

From Swedish patent application No. 76 033 968 an apparatus is further known for warming and moistening a dry respiration gas supplied to a patient, which has a housing and in the housing several discs at right angles to the direction of flow of the respiration gas, of which, in each case, one is moisture-absorbing as well as heatinsulating and the adjacent one is heat-conducting. In this apparatus, because of their small surface, the heat conducting discs cannot store heat to a sufficient degree.

SUMMARY OF THE INVENTION

The object underlying the invention is to create an apparatus of the type specified at the outset which is simple in construction and with which adequate warming and moistening even of a very dry inhalation gas is ensured.

According to the invention, this object is achieved by the fact that, provided in the housing, viewed in the direction of flow of the exhalation gas, there are lamellae whose interspaces are covered with the moisture store at the gas exit sides thereof. The lamellae have a large surface for storing large amounts of heat within a small space.

A particularly expedient development with compact, space-saving construction consists in the fact that the moisture store has a hollow cylindrical form and that the lamellae are designed in the form of discs disposed next to one another axially and adjoining a wall of the moisture store. Expediently, the lamellae can here be disposed in the interior of the moisture store and adjoin its inside wall, and at least one axial gas duct extending through the lamellae can be provided which runs to the end of the housing on the patient's side.

The invention is explained in more detail below with reference to a sample embodiment as illustrated in the accompanying sheet of drawings; other objects, features and advantages will be apparent from this detailed disclosure and from the appended claims.

BRIEF DESCRIPTION OF THE DRAWING

The single FIGURE is a somewhat diagrammatic longitudinal sectional view of an apparatus according to the present invention.

DETAILED DESCRIPTION

The Figure, shows, not to scale, an apparatus 1 for warming and moistening a respiration gas supplied to a patient. The apparatus 1 is fixed in a gas line 2 between a patient 3 and a respiration gas vessel 4. The apparatus 1 has a cylindrical housing 5 in which is fixed a hollow cylindrical moisture store 6. Lamellae 7 in the form of discs disposed next to one another axially are disposed in the interior of the moisture store 6. The interspaces between the lamellae 7 adjoin the inside wall 8 of the moisture reservoir or store 6 on the exit sides of the interspaces with respect to exhalation gas flow from the patient 3. Moreover, an axial gas duct 9 extending through the lamellae 7 is provided which runs to the end 10 of the housing 5 on the patient's side. Provided between the outside wall 11 of the housing 5 and the moisture store 6 is a gap or passage 12 which runs to the end 13 of the housing 5 on the gas vessel side. The moisture store 6 consists of a gas-permeable, hygroscopic material, e.g. viscocellulose with a mixture of cotton.

When the patient 3 exhales, the exhalation gas flows through the gas line 2 into the gas duct 9 and first accumulates between the lamellae 7. It then flows through the moisture store 6 which absorbs a large part of the moisture of the exhalation gas and passes via the air gap or passage 12 into a tube 14 whose free end opens into the atmosphere. At the end of the exhalation phase, warm and moist air is contained in the interspaces between the lamellae 7 in addition to the moisture and warmth stored in the moisture store 6. These interspaces therefore also act as warmth and moisture reservoirs or stores.

When the patient 3 inhales, dry inhalation gas flows from the respiratory vessel 4 via the gas line 2 into the air gap or passage 12 and, from there, through the moisture store 6 and between the lamellae 7. The dry gas takes up the warmth and moisture stored in the moisture reservoir 6 and that between the lamellae 7, with the result that the respiration gas supplied to the patient 3 which flows through the gas duct 9 and the gas line 2 contains the desired warmth and moisture.

It will be apparent that many modifications and variations may be effected without departing from the scope of the novel concepts and teachings of the present invention.

We claim as our invention:

1. Apparatus for warming and moistening a respiration gas for a patient, comprising a housing having a gas passage therethrough, said gas passage having a first fluid flow portion, one end of said first fluid flow portion including means for direct fluid flow communication with the mouth of the patient to receive exhalation gas flow from the patient when the patient exhales and for supplying a respiration gas to the patient when the patient inhales, the other end of said first fluid flow portion terminating within said housing, said gas passage having a second fluid flow having a second fluid flow portion, one end of said second fluid flow portion terminating within said housing and being in fluid communication with said other end of said first fluid flow passage, a respiration vessel connected with the gas passage and in fluid flow communication with the other end of said second fluid flow portion for supplying the respiration gas to said second fluid flow portion, means communicating with said other end of said second fluid flow portion for directing said exhalation gas flow from said patient to atmosphere, a moisture storage comprising gas-permeable, hygroscopic material in said gas passage, said other end of said first fluid flow portion comprising lamallae (7) disposed thereacross in the direction of flow of the exhalation gas, said lamellae (7) have interspaces in fluid flow communication with the first fluid flow portion at the gas inlet sides thereof, with said moisture storage (6) disposed over the exit sides thereof, whereby when the patient exhales, exhalation gas flows through the first fluid flow portion, the interspaces, the moisture storage, the second fluid flow portion to atmosphere and accumulates heat and moisture in said interspaces and in said moisture storage and when the patient inhales, inhalation gas flows from said respiratory vessel, through the second fluid flow portion, the moisture storage, the interspaces, the first fluid flow portion to the patient and collects the heat and moisture accumulated in the interspaces and moisture storage.

2. Apparatus according to claim 1, characterized in that the moisture store (6) has a hollow cylindrical form and that the lamellae (7) are constructed in the form of discs disposed in series axially and adjoining a wall of the moisture store (6).

3. Apparatus according to claim 2, characterized in that the lamellae (7) are disposed in the interior of the moisture store (6) and adjoin its inside wall (8), the lamellae (7) having at least one axial gas duct (9) extending therethrough comprising said first fluid flow portion which leads to an end (10) of the housing (5) on the patient's side.

4. Apparatus according to claim 2, characterized in that, said housing includes an outside wall (11) and wherein said outside wall and said moisture store (6) defines an annular gap comprising said second fluid flow portion.

* * * * *